United States Patent
Breuil et al.

(10) Patent No.: US 10,646,858 B2
(45) Date of Patent: May 12, 2020

(54) CATALYTIC COMPOSITION BASED ON CHROMIUM AND A LIGAND BASED ON PHOSPHINE AND ITS USE IN A METHOD FOR PRODUCING OCTENES

(71) Applicant: IFP Energies Nouvelles, Rueil-Malmaison (FR)

(72) Inventors: Pierre-Alain Breuil, Lyons (FR); David Proriol, Brignais (FR)

(73) Assignee: IFP Energies Nouvelles, Rueil-Malmaison (FR)

(*) Notice: Subject to any disclaimer, the term of this patent is extended or adjusted under 35 U.S.C. 154(b) by 0 days.

(21) Appl. No.: 16/306,037

(22) PCT Filed: May 17, 2017

(86) PCT No.: PCT/EP2017/061884
§ 371 (c)(1),
(2) Date: Nov. 30, 2018

(87) PCT Pub. No.: WO2017/207280
PCT Pub. Date: Dec. 7, 2017

(65) Prior Publication Data
US 2019/0168202 A1    Jun. 6, 2019

(30) Foreign Application Priority Data
May 31, 2016   (FR) ..................... 16 54932

(51) Int. Cl.
*B01J 31/18*   (2006.01)
*B01J 31/14*   (2006.01)
(Continued)

(52) U.S. Cl.
CPC .......... *B01J 31/188* (2013.01); *B01J 31/143* (2013.01); *B01J 31/1875* (2013.01); *C07C 2/32* (2013.01);
(Continued)

(58) Field of Classification Search
CPC .... B01J 31/188; B01J 31/1875; B01J 31/143; B01J 2231/20; B01J 2531/62; C07C 2/32;
(Continued)

(56) References Cited

U.S. PATENT DOCUMENTS

| 7,511,183 B2 | 3/2009 | Blann et al. |
| 9,487,456 B2 | 11/2016 | Overett et al. |

(Continued)

FOREIGN PATENT DOCUMENTS

| WO | 2004/056479 A1 | 7/2004 |
| WO | 2013/168106 A1 | 11/2013 |

OTHER PUBLICATIONS

International Search Report dated Jun. 19, 2017 issued in corresponding PCT/EP2017/061884 application (2 pages).

*Primary Examiner* — Ali Z Fadhel
(74) *Attorney, Agent, or Firm* — Millen White Zelano and Branigan, PC; John Sopp

(57) ABSTRACT

The invention pertains to a composition that comprises at least one chromium precursor, at least one heteroatomic ligand, and, optionally, at least one activator. The invention also pertains to the method for preparation of the composition in accordance with the invention and the use of said composition in a method for oligomerization of olefins.

9 Claims, 1 Drawing Sheet

(51) Int. Cl.
  *C07C 2/32* (2006.01)
  *C07C 2/36* (2006.01)
  *C07F 11/00* (2006.01)

(52) U.S. Cl.
  CPC ............... *C07C 2/36* (2013.01); *C07F 11/00* (2013.01); *B01J 2231/20* (2013.01); *B01J 2531/62* (2013.01); *C07C 2531/14* (2013.01); *C07C 2531/24* (2013.01)

(58) Field of Classification Search
  CPC ... C07C 2/26; C07C 2531/14; C07C 2531/24; C07F 11/00
  See application file for complete search history.

(56) References Cited

U.S. PATENT DOCUMENTS

| | | | | |
|---|---|---|---|---|
| 2006/0229480 | A1* | 10/2006 | Blann | B01J 31/2409 585/535 |
| 2015/0087873 | A1* | 3/2015 | Overett | C07C 2/36 585/513 |

* cited by examiner

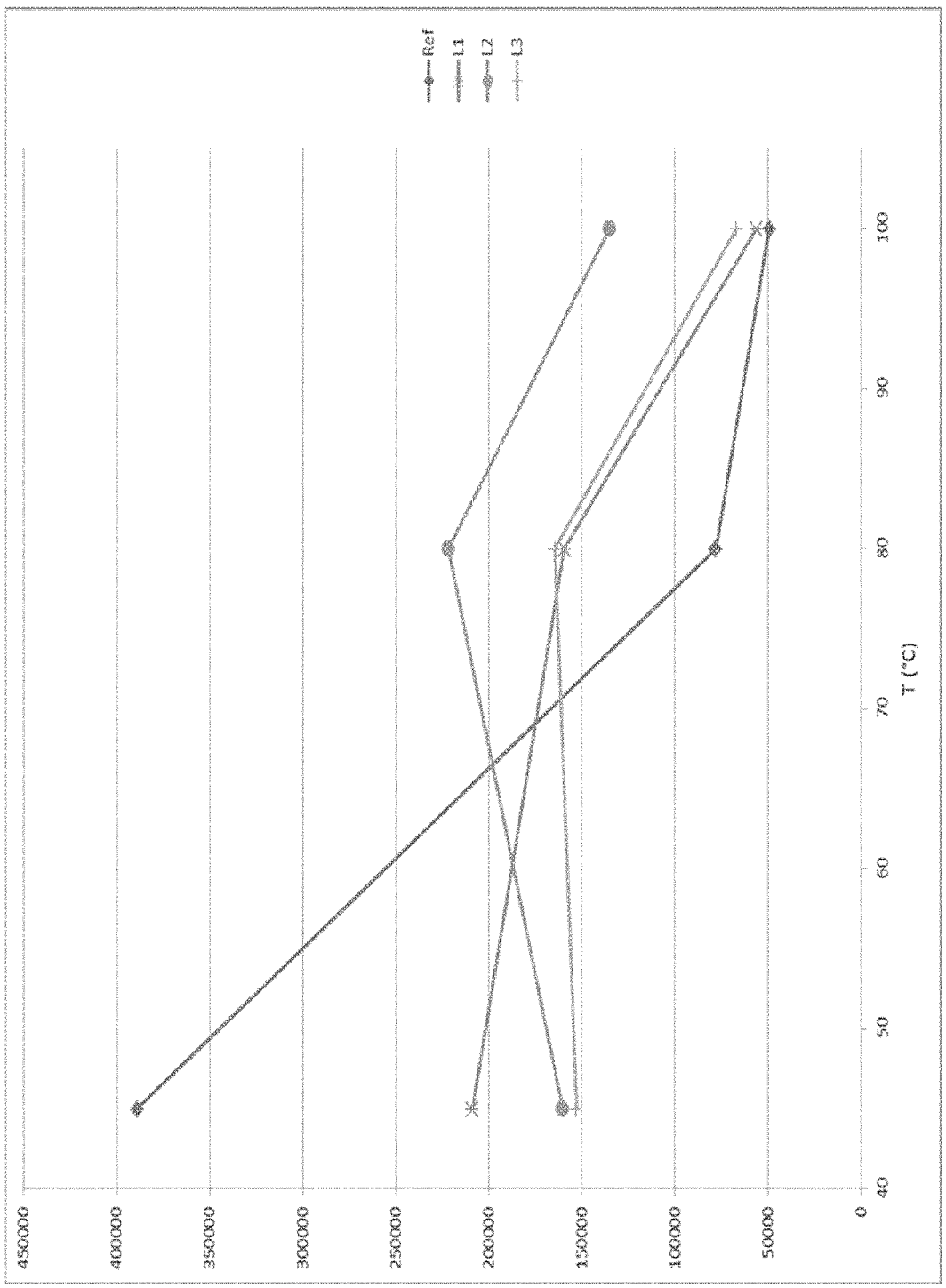

CATALYTIC COMPOSITION BASED ON CHROMIUM AND A LIGAND BASED ON PHOSPHINE AND ITS USE IN A METHOD FOR PRODUCING OCTENES

This invention describes a catalytic composition based on chromium and a particular ligand. The invention also pertains to the method for preparation of said composition, as well as its use in a method for producing octene from ethylene.

PRIOR ART

The catalytic compositions or systems based on chromium and ligands of the diphosphine type are known for catalyzing the selective conversion of ethylene into octene-1. The efficiency of such systems depends on the reaction conditions and the selection of the ligand structure. In particular, the nature and positions of all of the substituents of the ligand that is used have a decisive impact on the performance of the catalytic system.

The known catalytic compositions include examples of compositions based on chromium and the bis(phosphino) amine ligand of the "PNP" type. The article in J. Am. Chem. Soc. 2004, 126, 14712-14713 by Bollmann et al. and the applications of the WO2004/056479 A1 family report on the use of ligands that are described by the formula (R)nA-B-C(R)n, with A and C being selected from among the group comprising the atoms of phosphorus, arsenic, antimony, oxygen, bismuth, sulfur, selenium, or nitrogen, oxidized or not. These ligands are used for the reaction for tetramerization of ethylene into octene-1 under temperature conditions of 45° C. Among the long list of ligands cited, none is described as corresponding to the formula $(PR)_2N-X-O-PR_2$, with X being a divalent bridging group.

One of the drawbacks of these catalytic compositions is that it is necessary to employ them at a low temperature, i.e., at a temperature of between 45 and 60° C., because otherwise there is significant deactivation of the catalytic system as well as a loss of selectivity for octene-1. However, operation at a high temperature has the advantage that it makes it possible to achieve in particular an increase in the viscosity and thus the management of the heavy by-products that are formed.

To attempt to solve this problem, the patent applications WO2013/168102 A1 and WO2013/168106 A1 recently described the tetramerization of olefins at elevated temperatures, particularly above 80° C., done with catalytic systems based on ligands $R^1R^2P-X-PR^3R^4$, with groups $R^1$, $R^2$, $R^3$, and $R^4$, fluorinated or not, where X can be a group $N(R^6)$ in which $R^6$ is selected from among, i.a., the groups: alkyl, cycloalkyl, aryl, aryloxy, alkoxy, aminocarbonyl, and the silyl groups and derivatives thereof. None of the ligands described comprises the molecule fragment that corresponds to the structure $N(R^6)$, with $R^6$ corresponding to the formula-X—O—P—, with X being a divalent bridging group that is advantageously selected from among the alkylidenes. Moreover, the catalytic compositions described exhibited an octene-1 selectivity that was degraded at high temperature.

In his research, the applicant has developed a new catalytic composition that comprises at least one chromium precursor, at least one heteroatomic ligand that is described by the general formula (I) $(R^1)_2P-O-(CH_2)_n-N[P(R^2)_2]_2$, and at least one activator. The composition according to the invention demonstrated particularly advantageous catalytic properties, particularly in the olefin tetramerization reaction and more particularly in the reaction for tetramerization of ethylene into octene-1. Surprisingly enough, it was observed that the compositions according to the invention exhibit very good octene-1 productivity despite the fact that the tetramerization method is run at temperatures exceeding 60° C., or even 80° C.

An advantage of compositions according to the invention lies in the fact that they can be used in a tetramerization reaction under higher temperature conditions than the conventional compositions of the prior art without harming the octene-1 productivity of the catalytic system or its selectivity with respect to the production of octene-1.

DEFINITIONS

As used in this invention, the term "alkyl" is defined as a linear or branched hydrocarbon chain that has 1-15 carbon atoms and preferably 1-10 carbon atoms. Preferred alkyl groups are advantageously selected from among the groups: methyl, ethyl, propyl, isopropyl, butyl, isobutyl, tert-butyl, pentyl, and hexyl. These alkyl groups can be substituted by heteroelements or groups that contain heteroelements, such as a halide, an alkoxy. An "alkoxy" substituent is defined as an alkyl-O-group in which the term "alkyl" has the meaning given above. Preferred examples of alkoxy substituents are the groups methoxy or ethoxy.

The term "cyclic alkyl" is defined as a monocyclic hydrocarbon group that has more than 3 carbon atoms, preferably between 4 and 24, and in a more preferred manner between 5 and 18, preferably a cyclopentyl, cyclohexyl, cyclooctyl, or cyclododecyl group, or a polycyclic (bicyclic or tricyclic) group that has more than 3 carbon atoms and preferably between 5 and 18, such as, for example, the adamantyl or norbornyl groups. These groups can be substituted by heteroelements or groups containing heteroelements, such as a halide, an alkoxy.

The term "aromatic" is defined as an aromatic monocyclic or polycyclic group, substituted or not, preferably monocyclic or bicyclic, substituted or not, having between 5 and 20 carbon atoms. When the group is polycyclic, that is, it comprises more than one cyclic aromatic ring, the cyclic rings can advantageously be condensed two by two or attached two by two by a bonds. The aromatic group according to the invention can contain a heteroelement, such as nitrogen, oxygen, or sulfur. These groups can be substituted by heteroelements or groups containing heteroelements, such as a halide, an alkoxy.

SUMMARY DESCRIPTION OF THE INVENTION

This invention pertains to a composition that comprises:
at least one chromium precursor;
at least one heteroatomic ligand that is described by the general formula (I)

in which the groups $R^1$ and $R^2$, identical or not, bonded together or not, are selected from among the cyclic alkyl groups or not and the aromatic groups, and n is an integer greater than or equal to 1;
and, optionally, at least one activator.

Advantageously, according to the invention, the whole number n of the fragment —(CH2)n- of the ligand is between 1 and 15.

Advantageously, the molar ratio between the ligand and the chromium precursor is between 0.01 and 100.

Advantageously, the molar ratio between the activator and the chromium precursor is between 1 and 10,000.

Preferably, the chromium precursor is chosen from $CrCl_3$, $CrCl_3(tetrahydrofuran)_3$, $Cr(acetylacetonate)_3$, $Cr(naphthenate)_3$, $Cr(2-ethylhexanoate)_3$, $Cr(acetate)_3$.

Advantageously, the groups $R^1$ and $R^2$ of the ligand, identical or not, bonded together or not, are selected from a cyclic alkyl group or not, aromatic or not, having 1-15 carbon atoms.

Preferably, the groups $R^1$ and $R^2$, identical or not, bonded together or not, are selected from among the groups methyl, trifluoromethyl, ethyl, n-propyl, i-propyl, n-butyl, i-butyl, t-butyl, pentyl, cyclopentyl, hexyl, cyclohexyl, adamantyl, substituted or not, that may or may not contain heteroelements: the groups phenyl, o-tolyl, m-tolyl, p-tolyl, mesityl, 3,5-dimethylphenyl, 4-n-butylphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 2-chlorophenyl, 3-chlorophenyl, 4-chlorophenyl, 2-fluorophenyl, 3-fluorophenyl, 4-fluorophenyl, 4-trifluoromethylphenyl, 3,5-di(trifluoromethyl)phenyl, benzyl, naphthyl, bis-naphthyl, pyridyl, bis-phenyl, furanyl, thiophenyl, substituted or not, which may or may not contain heteroelements.

Advantageously, the activator agent is selected from among the tris(hydrocarbyl)aluminum compounds, the chlorinated or brominated hydrocarbylaluminum compounds, aluminum halides, aluminoxanes, organoboronated compounds, and organic compounds that are capable of providing a proton, taken individually or in a mixture.

The invention also pertains to the method for preparing the composition according to the invention, which involves bringing the following into contact:

at least one chromium precursor, with at least one heteroatomic ligand described by the general formula (I)

in which the groups $R^1$ and $R^2$, identical or not, bonded together or not, are selected from the cyclic alkyl groups or not and the aromatic groups, and n is an integer greater than or equal to 1;

and, optionally, with at least one activator.

Another aspect of the invention pertains to using the compositions according to the invention as catalysts.

Advantageously, the invention pertains to a method for tetramerization of ethylene into octene-1.

DETAILED DESCRIPTION OF THE INVENTION

Compositions According to the Invention

This invention pertains to a composition that comprises:
at least one chromium precursor,
with at least one heteroatomic ligand described by the general formula (I)

in which the groups $R^1$ and $R^2$, identical or not, bonded together or not, are selected from among the cyclic alkyl groups or not and the aromatic groups, and n is an integer greater than or equal to 1;

and, optionally, at least one activator.

The Chromium Precursor

The chromium precursor in accordance with the invention can be selected from among the chromium compounds used in the methods for oligomerization of olefins.

The chromium precursor that is present in the composition in accordance with the invention may comprise one or more identical or different anions that are selected from among the group made up of halides, carboxylates, acetylacetonates, and the alkoxy and aryloxy anions. The chromium compound can be a salt of chromium(II) or chromium(III), but also a salt with a different degree of oxidation that can comprise one or more identical or different anions, such as, for example, halides, carboxylates, acetylacetonates, and alkoxy or aryloxy anions. The chromium precursors used preferably in the invention are compounds of chromium(III) because they are more accessible, but a compound of chromium(I) or chromium(II) may also be suitable.

Preferably, according to the invention, the chromium precursor is selected from among $CrCl_3$, $CrCl_3(tetrahydrofuran)_3$, $Cr(acetylacetonate)_3$, $Cr(naphthenate)_3$, $Cr(2-ethylhexanoate)_3$, $Cr(acetate)_3$.

The Heteroatomic Ligand

The ligand of the catalytic composition according to the invention is described by the general formula (I)

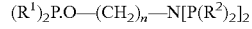

in which the groups $R^1$ and $R^2$, identical or not, bonded together or not, are selected from among the cyclic alkyl groups or not and the aromatic groups, and n is an integer greater than or equal to 1.

The whole number n of the fragment —$(CH_2)_n$— of the ligand according to the invention is preferably between 1 and 15, in a more preferred manner between 2 and 15, in an even more preferred manner between 2 and 10, and even more preferably between 3 and 6.

According to the invention, the groups $R^1$ and $R^2$, identical or not, bonded together or not, are selected from among a cyclic alkyl group or not having 1-15 carbon atoms, preferably 1-10 carbon atoms, or an aromatic group having a number of carbons of greater than 3, preferably between 4 and 24, and in an even more preferred manner between 5 and 18.

Preferably, the groups $R^1$ and $R^2$, identical or not, bonded together or not, are selected from among the groups methyl, trifluoromethyl, ethyl, n-propyl, i-propyl, n-butyl, i-butyl, t-butyl, pentyl, cyclopentyl, hexyl, cyclohexyl, adamantyl, substituted or not, that may or may not contain heteroelements; the groups phenyl, o-tolyl, m-tolyl, p-tolyl, mesityl, 3,5-dimethylphenyl, 4-n-butylphenyl, 2-methoxyphenyl, 3-methoxyphenyl, 4-methoxyphenyl, 2-isopropoxyphenyl, 4-methoxy-3,5-dimethylphenyl, 3,5-di-tert-butyl-4-methoxyphenyl, 2-chlorophenyl, 3-chlorophenyl, 4-chlorophenyl, 2-fluorophenyl, 3-fluorophenyl, 4-fluorophenyl, 4-trifluoromethylphenyl, 3,5-di(trifluoromethyl)phenyl, benzyl, naphthyl, bis-naphthyl, pyridyl, bis-phenyl, furanyl, thiophenyl, substituted or not, may or may not contain heteroelements.

In one particular implementation, the groups $R^1$ and $R^2$, identical or not, bonded together or not, are selected from among the groups methyl, ethyl, i-propyl, n-butyl, i-butyl, t-butyl, cyclopentyl, and cyclohexyl.

In one particular implementation, the groups $R^1$ and $R^2$, identical or not, bonded together or not, are selected from among the groups phenyl, o-tolyl, m-tolyl, p-tolyl, mesityl, 2-methoxyphenyl, 3-methoxyphenyl, 4-methoxyphenyl, 2-chlorophenyl, 3-chlorophenyl, 4-chlorophenyl, 2-fluorophenyl, 3-fluorophenyl, 4-fluorophenyl.

The Activator Agent

The composition according to the invention can include an activator agent. The activator agent can be selected from among the compounds known to one skilled in the art. Mixtures of activator agents may also be used.

Advantageously, the activator agents according to the invention are selected from among the tris(hydrocarbyl) aluminum compounds, the chlorinated or brominated hydrocarbylaluminum compounds, aluminum halides, aluminoxanes, organoboronated compounds, and organic compounds that are capable of providing a proton, taken individually or in a mixture.

Among the derivatives of aluminum, the following can be cited: the alkylaluminum halides, such as dimethylaluminum chloride, diethylaluminum chloride, ethylaluminum dichloride, methylaluminum sesquichloride, ethylaluminum sesquichloride, methylaluminum dichloride, isobutylaluminum dichloride, aluminum trichloride; and aluminoxanes, used individually or in a mixture.

The aluminoxanes are well known to one skilled in the art as oligomeric compounds that can be prepared by the controlled addition of water to an alkylaluminum, for example trimethylaluminum. Such compounds may be linear, cyclic, or mixtures of these compounds. They are generally represented by the formula [RAlO]a, where R is a hydrocarbon group and a is a number from 2 to 50. Preferably, the aluminoxane is selected from among methylaluminoxane (MAO) and/or ethylaluminoxane (EAO) and/or from among the modified aluminoxanes such as the modified methylaluminoxane (MMAO).

In the case where said activator agent is selected from among the organoboronated compounds, said activator agent is preferably selected from among the Lewis acids of the tris(aryl)borane type, such as tris(perfluorophenyl)borane, tris(3,5-bis(trifluoromethyl)phenyl)borane, tris(2,3,4,6-tetrafluorophenyl)borane, tris(perfluoronaphthyl)borane, tris(perfluorobiphenyl)borane and derivatives thereof, and the (aryl)borates associated with a triphenylcarbenium cation or with a trisubstituted ammonium cation, such as triphenylcarbenium tetrakis(perfluorophenyl)borate, N,N-dimethylanilinium tetrakis(perfluorophenyl)borate, N,N-diethylanilinium tetrakis(3,5-bis(trifluoromethyl)phenyl)borate, and triphenylcarbenium tetrakis(3,5-bis(trifluoromethyl)phenyl)borate.

In the case where said activator agent is selected from among the organic compounds that are capable of providing a proton, said activator agent is preferably selected from among the acids of formula HY, in which Y represents an anion, such as $HBF_4$ or $F_3CSO_3H$.

Preparation of the Compositions According to the Invention

Another object of the invention pertains to the method for preparing compositions according to the invention.

The compositions according to the invention are preferably prepared by bringing the following into contact:
at least one chromium precursor,
with at least one heteroatomic ligand described by the general formula (I)

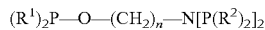

in which the groups $R^1$ and $R^2$, identical or not, bonded together or not, are selected from among the cyclic alkyl groups or not and the aromatic groups, and n is an integer greater than or equal to 1,
and, optionally, with at least one activator.

In one particular embodiment, the molar ratio between the ligand and the chromium precursor is between 0.01 and 100, and preferably between 0.5 and 5, in particular between 0.8 and 3.

When the activator is present in the composition, the molar ratio between the activator and the chromium precursor is between 1 and 10,000, preferably between 100 and 5,000, and in an even more preferred manner between 200 and 3,500.

During the preparation method, the components of the composition can be added simultaneously or in sequence, in any order. The composition according to the invention can be prepared in situ with the feedstock, particularly ethylene, being either present or absent.

The compositions according to the invention can be in the presence of a solvent or not. It is possible to use a solvent that is advantageously selected from among the solvents that are capable of dissolving the reagents. To do this, the use of organic solvents is preferred. These include the aliphatic hydrocarbon solvents that are saturated or not, such as pentane, hexane, cyclohexane, methyl cyclohexane, or heptane, cyclohexene, cyclooctene, or cyclooctadiene. Aromatic solvents that can be mentioned include benzene, toluene, or xylenes. Oxidized solvents that can be mentioned include diethyl ether or tetrahydrofuran and chlorinated solvents such as dichloromethane or chlorobenzene. These solvents can be used by themselves or in a mixture.

The temperature at which the components of the composition according to the invention are mixed is advantageously between −40 and +150° C. and preferably between 0 and +80° C., for example at a temperature close to room temperature (15-30° C.). The mixture can be made under an atmosphere of ethylene or inert gas.

Use of the Compositions According to the Invention

Another object of the invention pertains to using compositions according to the invention as catalysts.

The compositions according to the invention can be used as catalysts in a chemical transformation reaction, in particular in an oligomerization method that involves bringing said feedstock comprising olefins having between 2 and 10 carbon atoms into contact with the composition according to the invention, where said method is advantageously run at a total pressure of between atmospheric pressure and 20 MPa and at a temperature of between −40 and +250° C.

The composition according to the invention is advantageously employed in a method for tetramerization of olefins, in particular in a method for tetramerization of ethylene into octene-1.

The solvent of the oligomerization method can be selected from among organic solvents and preferably from among ethers, alcohols, chlorinated solvents, and saturated or unsaturated hydrocarbons, aromatic or not, cyclic or not. In particular, said solvent is selected from among hexane, cyclohexane, methylcyclohexane, heptane, butane, or isobutane, where the monoolefins or diolefins preferably comprise 4-20 carbon atoms, benzene, toluene, orthoxylene, mesitylene, ethylbenzene, dichloromethane, chlorobenzene, methanol, ethanol, in pure form or in a mixture, and the ionic liquids. In the case where said reaction solvent is an ionic liquid, it is advantageously selected from among the ionic liquids described in the patents U.S. Pat. No. 6,951,831 B2 and FR 2895406 B1.

Oligomerization is defined as the transformation of a monomer unit into a compound or a mixture of compounds having the general formula $C_pH_{2p}$ with 4≤p≤80, preferably with 4≤p≤50, in a preferred manner with 4≤p≤26, and in a more preferred manner with 4≤p≤14.

The olefins used in the method of oligomerization are olefins that comprise 2-10 carbon atoms. Preferably, said olefins are selected from among ethylene, propylene, n-butenes, and n-pentenes, by themselves or in a mixture, pure or dilute.

In the case where said olefins are dilute, said olefins are diluted with one or more alkane(s), such as those found in "fractions" resulting from petroleum refining methods, such as catalytic cracking or steam cracking.

In a preferred manner, the olefin used in the oligomerization method and, in particular, in the tetramerization method according to the invention is ethylene.

Said olefins can come from non-fossil resources such as biomass. For example, the olefins used in the oligomerization method according to the invention and, in particular, in the tetramerization method according to the invention can be produced from alcohols, and in particular by the dehydration of alcohols.

The oligomerization method, in particular the tetramerization method according to the invention, advantageously operates at a total pressure of between atmospheric pressure and 20 MPa, preferably between 0.1 and 8 MPa, and at a temperature of between −40 and +250° C., preferably between 0 and 150° C., preferably between 20 and 135° C., preferably between 45 and 100° C., preferably between 75 and 100° C., and preferably between 80 and 100° C.

The heat that is generated by the reaction can be eliminated by any means known to one skilled in the art.

The oligomerization method, in particular the tetramerization method according to the invention, can be carried out in a closed system, a semi-open system, or continuously, with one or more reaction stages. Vigorous stirring is advantageously employed to ensure good contact between the reagent(s) and the catalytic system.

The products obtained from this method can be used, for example, as components in plastics and more particularly polyethylene, fuels for motor vehicles, as feedstocks in a hydroformylation method for synthesizing aldehydes and alcohols, as components for the chemical industry, pharmaceutical industry, perfume-making and/or as feedstocks in a metathesis method for the synthesis of, for example, propylene.

The following examples illustrate the invention without limiting its scope.

EXAMPLES

Synthesis of Ligands
Ligand L1

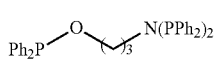

30 mL of dichloromethane (CH$_2$Cl$_2$), 6 mL of triethylamine (44.4 mmol), and 2.71 g (12.3 mmol) of Ph$_2$PCl are introduced into a 100-mL Schlenk. At 0° C., 0.256 g (3.4 mmol) of 3-aminopropanol is added. The mixture is allowed to stir for 2 hours at room temperature. The solvent is evaporated. The product is extracted with pentane, and the pentane is then evaporated under a vacuum. The product is purified on an alumina column with a mixture of dichloromethane/pentane at a ratio of 30/70 (volume/volume). 0.4 g of a very viscous, whitish oil is obtained, i.e., a yield of approximately 19%.
NMR $^1$H (300.1 MHz, CD$_2$Cl$_2$); δ (ppm): 7.55-7.12 (m, 30H); 3.48 (m, 2H); 3.41 (m, 2H); 1.55-1.40 (m, 2H); NMR $^{31}$P (121.5 MHz, CD$_2$Cl$_2$); δ (ppm): 111.4; 63.4; NMR $^{13}$C (75.5 MHz, CD$_2$Cl$_2$); δ (ppm): 142.6; 140.0; 133.1; 130.4; 129.6; 129.2; 128.6; 128.5; 68.2; 50.7; 33.6.

Ligand L2

60 mL of CH$_2$Cl$_2$, 3.0 g (29.6 mmol) of triethylamine, and 4.37 g (19.8 mmol) of Ph$_2$PCl are introduced into a 100-mL Schlenk. At 0° C., 0.54 g (6.0 mmol) of 4-aminobutanol is added. The mixture is allowed to stir for one night at room temperature. The solvent is filtered and then evaporated. The triethylamine is eliminated by co-evaporation with toluene. Purification is then done by recrystallization in ethanol. Approximately 1 g of a very viscous oil is obtained, i.e., a yield of approximately 26%.
NMR $^1$H (300.1 MHz, CD$_2$Cl$_2$); δ (ppm): 7.55-7.27 (m, 30H); 3.54 (m, 2H); 3.31 (dt, 2H); 1.44-1.27 (m, 2H); 1.27-1.13 (m, 2H); NMR $^{13}$C (75.5 MHz, CD$_2$Cl$_2$); δ (ppm): 142.8; 140.1; 133.1; 130.4; 129.5; 129.1; 128.6; 128.5; 70.0; 53.1; 29.1; 28.5; NMR $^{31}$P (121.5 MHz, CD$_2$Cl$_2$); δ (ppm): 110.4; 62.6.

Ligand L3

0.436 g (3.72 mmol) of 6-aminohexanol is weighed into a Schlenk. 6 mL (44.45 mmol) of triethylamine and 30 mL of dichloromethane (CH$_2$Cl$_2$) are added. At 0° C., 1.81 g (8.20 mmol) of Ph$_2$PCl is added drop by drop. The mixture is allowed to stir for 2 hours at room temperature. The volatile products are filtered and then evaporated. Extraction is done with 6 times 7 mL of pentane. The solvent is eliminated under vacuum. 1.2 g of a yellowish, very viscous oil is obtained, i.e., a yield of approximately 66%.
NMR $^1$H (300.1 MHz, CD$_2$Cl$_2$); δ (ppm): 7.53-7.22 (m, 30H); 3.71 (m, 2H); 3.23 (m, 2H); 1.44 (m, 2H); 1.06 (m, 4H); 0.91 (m, 2H). NMR $^{31}$P (121.5 MHz, CD$_2$Cl$_2$); δ (ppm): 110.6; 62.5; NMR $^{13}$C (75.5 MHz, CD$_2$Cl$_2$); δ (ppm): 143.0; 140.2; 133.1; 130.4; 129.5; 129.1; 128.7; 128.4; 70.4; 53.4; 31.7; 31.6; 26.7; 25.7.

Catalytic Tests

The ligands L1, L2, and L3 are evaluated in the presence of Cr(acac)$_3$ (acac=acetylacetonate) for the ethylene tetramerization reaction. The molar ratio between the ligand and chromium is 2. The activator agent used is methylaluminoxane (MAO) at a molar ratio of MAO to the precursor Cr(acac)$_3$ of 600. The reaction is run under 4.5 MPa of ethylene. The ligands are evaluated at three different temperatures, i.e., 45° C., 80° C., and 100° C.

The ligand Ref below is used for comparison and is evaluated under the same conditions as the ligands L1, L2, and L3.

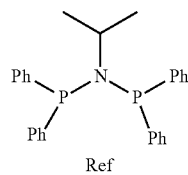 [SMILES: CC(C)N(P(c1ccccc1)c1ccccc1)P(c1ccccc1)c1ccccc1]

Ref

Operating Conditions: A 100-mL reactor is placed under ethylene pressure. The reaction solvent is introduced into the reactor as well as the MAO (10% by weight in toluene). The reactor is then put under 0.5 MPa of ethylene and is stirred for 5 minutes. After depressurization, the solution that is formed by the chromium precursor Cr(acac)$_3$ and the ligand is then introduced into the reactor. The reactor is then placed under 2 MPa of ethylene pressure and is heated to the test temperature. The pressure is finished off at 4.5 MPa, and stirring at 1,000 RPM is initiated. The system is then monitored for pressure.

At the end of the test, the ethylene feed is cut off, and the reactor is cooled. Once the reactor has been degassed, the liquid phase and the polymer that is optionally formed are recovered and weighed. The polymer is weighed after drying at 100° C. for one night. The liquid phase is then neutralized with a 10% by weight sulfuric acid solution. The analysis of the liquid phase is done by gas phase chromatography with a GC HP 685 that is equipped with a column of the PONA brand.

The results of the experiments are presented in the table below. The ethylene consumption described in the table corresponds to the quantity (in grams) of ethylene that is transformed during the catalytic test into reaction products. The activity described in g/(g$_{Cr}$.h) in the table corresponds to the quantity of ethylene (in grams) that is transformed by 1 g of chromium obtained from the catalytic composition relative to one hour of reaction.

FIG. 1 depicts the changes in C8 productivity as a function of the reaction temperature. The C8 productivity described in FIG. 1 corresponds to the quantity of octenes (in grams) that is transformed by 1 g of chromium obtained from the catalytic composition relative to one hour of reaction. Said productivity is calculated by multiplying the activity by the percentage of C8 that is the weight percentage of C8 with respect to the products formed.

| Ligand | Temp. (° C.) | Tps (min) | Consumption of C$_2$H$_4$ (g) | Activity (g/(g$_{Cr}$.h)) | C$_6$ % C$_6$$^a$ | % 1-C$_6$$^b$ | C$_8$ % C$_8$$^a$ | % 1-C$_8$$^c$ | PE %$^a$ | (mg) |
|---|---|---|---|---|---|---|---|---|---|---|
| Ref* | 45 | 8 | 21.5 | 621 | 21.2 | 76.0 | 62.6 | 98.8 | 1.0 | 210 |
| Ref* | 80 | 30 | 18.1 | 140 | 33.2 | 88.6 | 55.8 | 99.1 | 1.6 | 283 |
| Ref* | 100 | 30 | 16.2 | 125 | 46.1 | 93.9 | 39.6 | 98.9 | 3.7 | 569 |
| L1 | 45 | 8 | 17.3 | 494 | 14.7 | 31.5 | 42.3 | 93.7 | 14.0 | 2,259 |
| L1 | 80 | 15 | 18.2 | 278 | 27.9 | 66.3 | 57.4 | 97.4 | 1.3 | 228 |
| L1 | 100 | 30 | 16.6 | 127 | 38.6 | 84.3 | 44.3 | 97.9 | 4.0 | 628 |
| L2 | 45 | 15 | 21.1 | 321 | 16.7 | 35.6 | 50.0 | 94.4 | 8.3 | 1,615 |
| L2 | 80 | 10 | 16.7 | 380 | 27.4 | 66.6 | 58.4 | 97.5 | 2.2 | 334 |
| L2 | 100 | 15 | 19.5 | 296 | 38.3 | 82.8 | 45.7 | 97.8 | 3.0 | 562 |
| L3 | 45 | 8 | 10.0 | 288 | 14.7 | 32.9 | 53.1 | 95.2 | 5.2 | 497 |
| L3 | 80 | 15 | 7.8 | 274 | 27.3 | 68.4 | 60.1 | 97.8 | 1.5 | 260 |
| L3 | 100 | 30 | 19.9 | 153 | 36.0 | 83.5 | 43.8 | 97.9 | 7.8 | 1,437 |

Reaction conditions: Cr(acac)$_3$, n$_{Cr}$ = 5 μmol; Ligand/Cr = 2, (MAO/Cr = 600); Solvent = Cyclohexane (50 mL), Pressure = 4.5 MPa of C$_2$H$_4$.
*= Comparison example.
$^a$% = Percent by weight relative to products formed.
$^b$% 1-C$_6$: Percentage of hexene-1 in the C$_6$ fraction.
$^c$%1-C$_8$: Percentage of octene-1 in the C$_8$ fraction.
PE = Polyethylene,
Temp. = Temperature,
Tps = Time.

We observe that the compositions according to the invention make it possible to increase significantly the proportion of C8 (% C8) relative to the other products that are formed when the temperature is raised from 45° C. to 80° C. In particular, at 80° C., it can be noted that the C8 productivity observed with the compositions (with L1, L2, and L3) according to the invention is thus considerably superior to that observed with the composition used as a comparison example (Ref).

The invention claimed is:

1. Composition comprising:
   at least one chromium precursor,
   at least one heteroatomic ligand described by the general formula (I)

   $$(R^1)_2P\text{—}O\text{—}(CH_2)_n\text{—}N[P(R^2)_2]_2$$

in which the groups $R^1$ and $R^2$, identical or not, bonded together or not, are selected from among cyclic, linear, or branched alkyl groups or aromatic groups, and n is an integer greater than or equal to 1 and less than or equal to 15; and, optionally, at least one activator.

2. Composition in accordance with claim 1, in which the molar ratio between the ligand and the chromium precursor is between 0.01 and 100.

3. Composition in accordance with claim 1, in which the molar ratio between the activator and the chromium precursor is between 1 and 10,000.

4. Composition in accordance with claim 1, in which the chromium precursor is selected from among CrCl$_3$, CrCl$_3$(tetrahydrofuran)$_3$, Cr(acetylacetonate)$_3$, Cr(naphthenate)$_3$, Cr(2-ethylhexanoate)$_3$, and Cr(acetate)$_3$.

5. Composition in accordance with claim 1, in which activator agent is selected from among the tris(hydrocarbyl) aluminum compounds, the chlorinated or brominated compounds of hydrocarbylaluminum, aluminum halides, aluminoxanes, the organoboronated compounds, and the organic compounds that are capable of providing a proton, taken individually or in a mixture.

6. Method for preparing the composition according to claim 1, comprising bringing the following into contact:
   the at least one chromium precursor;
   with the at least one heteroatomic ligand that is described by the general formula (I)
   and, optionally, with the at least one activator.

7. Method in accordance with claim 6, in which the brining into contact is carried out at a temperature of between −40° C. and +150° C.

8. Method for oligomerization of an olefinic feedstock that comprises olefins having between 2 and 10 carbon atoms comprising:
   oligomerizing the olefinic feedstock with the composition in accordance with claim 1, wherein the oligomerizing is run at a total pressure of between atmospheric pressure and 20 MPa and at a temperature of between −40° C. and +250° C.

9. Method in accordance with claim 8, in which the method is a method for tetramerization of ethylene into octene-1.

* * * * *